United States Patent [19]
Saint-Leger

[11] Patent Number: 5,919,438
[45] Date of Patent: *Jul. 6, 1999

[54] DERMATOLOGICAL/COSMETIC COMPOSITIONS COMPRISING ANTIFUNGAL AND ANTIBACTERIAL COMPOUNDS AND REDUCTION OF HAIR LOSS THEREWITH

[75] Inventor: Didier Saint-Leger, Courbevoie, France

[73] Assignee: Societe L'Oreal S.A., Paris, France

[ * ] Notice: This patent is subject to a terminal disclaimer.

[21] Appl. No.: 08/838,137

[22] Filed: Apr. 15, 1997

Related U.S. Application Data

[63] Continuation of application No. 08/435,806, May 5, 1995, Pat. No. 5,650,145.

[30] Foreign Application Priority Data

May 5, 1994 [FR] France ................................. 94 05541

[51] Int. Cl.⁶ ..................................................... A61K 7/06
[52] U.S. Cl. .................. 424/70.1; 424/70.8; 424/DIG. 5; 514/880; 514/881; 514/937; 514/945; 514/944; 514/969
[58] Field of Search .................................. 424/70.1, 70.8, 424/DIG. 5; 514/880, 881, 937, 944, 945, 969

[56] References Cited

U.S. PATENT DOCUMENTS 5,650,145  7/1997  Saint-Leger ............................ 424/70.1

FOREIGN PATENT DOCUMENTS

| 2618068 | 1/1989 | France . |
| 2685867 | 7/1993 | France . |
| 2694694 | 2/1994 | France . |
| 2197194 | 5/1988 | United Kingdom . |
| 2207051 | 1/1989 | United Kingdom . |
| 9307847 | 4/1993 | WIPO . |

OTHER PUBLICATIONS

Reynolds, J.E.F. (Ed.), 'Martindale: The Extra Pharmacopoeia' (Electronic Version, Micromedex, Inc., Denver, "Sebo Shampooing".
Reynolds, J.E.F. (Ed.), 'Martindale: The Extra Pharmacopoeia' (Electronic Version, Micromedex, Inc., Denver, "Spectro Tar".
Reynolds, J.E.F. (Ed.), 'Martindale: The Extra Pharmacopoeia' (Electronic Version, Micromedex, Inc., Denver, "Teerol–H".
Reynolds, J.E.F. (Ed.), 'Martindale: The Extra Pharmacopoeia' (Electronic Version, Micromedex, Inc., Denver, "Denorex".
Reynolds, J.E.F. (Ed.), 'Martindale: The Extra Pharmacopoeia' (Electronic Version, Micromedex, Inc., Denver, "Ionil–T".
V–I Vademecum Internacional, Medicom S.A., Madrid, 1993, "Sebumselen".
Reynolds, J.E.F. (Ed.), 'Martindale: The Extra Pharmacopoeia' (Electronic Version, Micromedex, Inc., Denver, "Mycota".
Reynolds, J.E.F. (Ed.), 'Martindale: The Extra Pharmacopoeia' (Electronic Version, Micromedex, Inc., Denver, "Quinortar".
Reynolds, J.E.F. (Ed.), 'Martindale: The Extra Pharmacopoeia' (Electronic Version, Micromedex, Inc., Denver, "Pima Biciron".
Reynolds, J.E.F. (Ed.), 'Martindale: The Extra Pharmacopoeia' (Electronic Version, Micromedex, Inc., Denver, "Timoped".
Reynolds, J.E.F. (Ed.), 'Martindale: The Extra Pharmacopoeia' (Electronic Version, Micromedex, Inc., Denver, "Mycil".
Reynolds, J.E.F. (Ed.), 'Martindale: The Extra Pharmacopoeia' (Electronic Version, Micromedex, Inc., Denver, "Nystaform".

*Primary Examiner*—Jyothsna Venkat
*Attorney, Agent, or Firm*—Burns, Doane, Swecker & Mathis, L.L.P.

[57] ABSTRACT

Dermatological/cosmetic compositions for reducing or decelerating human hair loss comprise an effective hair loss-reducing amount of combinatory immixture of (a) at least one antifungal agent and (b) at least one halogenated antibacterial agent other than a macrolide or pyranoside, characteristically formulated in a topically physiologically acceptable medium therefor.

8 Claims, No Drawings

DERMATOLOGICAL/COSMETIC COMPOSITIONS COMPRISING ANTIFUNGAL AND ANTIBACTERIAL COMPOUNDS AND REDUCTION OF HAIR LOSS THEREWITH

This application is a continuation of application Ser. No. 08/435,806, filed May 5, 1995, now U.S. Pat. No. 5,650,145.

BACKGROUND OF THE INVENTION

1. Technical Field of the Invention

The present invention relates to novel dermatological/cosmetic compositions comprising at least one antifungal agent and at least one halogenated antibacterial agent, other than those of the genera macrolide and pyranoside, and to topical applications thereof for the reduction of hair loss.

2. Description of the Prior Art

It has long been known to this art that natural hair loss in humans reflects the overall equilibrium of hair follicles between the alternating growth phases (anagenic phases) and the hair loss phases (telogenic phases). The average ratio of the number of follicles in the anagenic phase to that in the telogenic phase is on the order of 9 (90/10). The percentage of follicles in the rest or quiescent phase (catagenic phase) appears to be very low.

Natural hair loss may be estimated, on average, to be a few hundred hairs per day for a normal physiological state. For a pathological physiological state, this number may attain a value of several hundred per day, leading to alopecia.

Moreover, a microbiological flora exists at the surface of the scalp, this flora consisting naturally of bacteria and yeasts. When an imbalance occurs in the natural composition of this flora, hair loss may be increased.

It too is known, moreover, that certain factors such as hormonal imbalance, physiological stress or food deficiencies may accelerate the phenomenon.

In order to reduce hair loss, FR-2,618,068 describes treatment of the scalp with a composition containing an antifungal agent which is optionally combined with an anti-inflammatory agent and/or with an antibiotic agent selected from among the macrolides or the pyranosides. However, such compositions are not entirely satisfactory since, although the reduction of hair loss is more pronounced than with treatment using an antifungal agent alone, topical application of anti-inflammatory agents have a tendency to bring about variations in the natural composition of the microbiological flora, thereby increasing the risks of infection.

Antibiotic agents are not entirely satisfactory either, since they are often unstable in cosmetic or dermatological compositions. In addition, they promote bacterial resistance phenomena, thus resulting in lesser effectiveness of the compositions intended to reduce or decelerate hair loss.

The topical application of antibacterial agents does not promote these resistance phenomena, but it appears that most of the conventional antibacterial agents inhibit the action of antifungal agents, thereby also reducing the effectiveness of compositions containing this type of combination.

SUMMARY OF THE INVENTION

It has now unexpectedly been determined that compositions intended to reduce or decelerate hair loss and containing an antifungal agent are more effective when this agent is combined with a halogenated antibacterial agent not of the macrolide and pyranoside families; surprisingly, these halogenated antibacterial agents do not inhibit the action of antifungal agents as is the case with the nonhalogenated antibacterial agents.

In addition, such halogenated antibacterial agents are very stable when they are formulated into the compositions of the invention and they promote no bacterial resistance.

Briefly, the present invention thus features novel dermatological/cosmetic compositions comprising at least one antifungal agent and at least one halogenated antibacterial agent, other than those of the genera macrolide and pyranoside, and to topical applications thereof for the reduction of hair loss.

DETAILED DESCRIPTION OF BEST MODE AND PREFERRED EMBODIMENTS OF THE INVENTION

More particularly according to the present invention, it is observed that after a few weeks of treatment, the appearance of the hair is improved, and the hair is, in particular, shinier, lighter and less greasy.

According to the invention, by the term "antifungal agent" is intended any substance capable of inhibiting or preventing the growth of yeasts, in particular those found at the surface of the epidermis which is rich in sebaceous glands and especially at the surface of the scalp such as, for example, *Pityrosporum ovale* and varieties thereof (*Pityrosporum orbiculare* and *Malassezia furfur*).

Among the antifungal agents suitable for formulation according to the invention, particularly representative are terbinafine, zinc pyrithione, selenium sulfide, tars and derivatives thereof, undecylenic acid and salts thereof and hydroxypyridone derivatives such as CICLOPIROX, i.e., 6-cyclohexyl-1- hydroxy-4-methyl-2-(1H)-pyridone, or OCTOPIROX, i.e., 1-hydroxy-4-methyl-6-(2,4,4-trimethylpentyl)- 2-(1H)-pyridone.

These antifungal agents are preferably present in the compositions in accordance with this invention at a concentration ranging from 0.01% to 5% by weight approximately relative to the total weight of the composition. Even more preferably, the concentration of antifungal agents may range from 0.1% to 2% by weight relative to the total weight of the composition.

Also according to the invention, by the term "halogenated antibacterial agent" is intended any substance containing at least one halogen atom and capable of inhibiting or preventing the growth of the bacterial flora present at the surface of epidermis which is rich in sebaceous glands.

The halogenated antibacterial agents according to the present invention are preferably benzene derivatives.

Among the halogenated antibacterial agents suitable for formulation according to the invention, particularly exemplary are chlorinated antibacterial agents such as triclosan, i.e., 5-chloro-2-(2,4- dichlorophenoxy)phenol, marketed under the trademark IRGASAN by Ciba-Geigy, chlorhexidine and derivatives thereof, chloramphenicol and 1-(4-chlorophenoxy)-1-(1H- imidazolyl)-3,3-dimethyl-2-butanone, marketed under the trademark CLIMBAZOLE by Bayer. These halogenated antibacterial agents are preferably present in the compositions in accordance with the invention at a concentration which may range from 0.01% to 10% by weight approximately relative to the total weight of the composition. Even more preferably, the concentration of antibacterial agents may range from 0.1% to 2% by weight relative to the total weight of the composition.

The weight ratio of the antifungal agents to the halogenated antibacterial agents may vary over wide limits. In particular, this weight ratio preferably ranges from 0.2 to 10.

The compositions in accordance with this invention may be in various forms typically employed in cosmetics or in dermatology for the treatment of the scalp.

They may, more particularly, be formulated with a topically physiologically (dermatologically/cosmetically) acceptable vehicle, carrier or diluent in the form of lotions, shampoos, foams, creams, gels, sticks, sprays, balms, ointments, milks, salves, emulsions, powders, or solid or liquid soaps.

The physiologically acceptable medium generally comprises water or of a mixture of water and at least one organic solvent which is physiologically acceptable for the purpose of a topical application. Among these solvents, exemplary are acetone, $C_1$–$C_4$ lower alcohols such as ethanol and isopropyl alcohol, alkylene glycols such as ethylene glycol and propylene glycol, ethylene glycol monomethyl, monoethyl or monobutyl ethers, the monoethyl ethers of propylene glycol and of dipropylene glycol, the $C_1$–$C_4$ alkyl esters of short-chain acids and polytetrahydrofuran ethers. When these are indeed present, such solvents preferably constitute from 1% to 80% by weight of the total weight of the composition.

The medium may be thickened using thickening agents typically employed in cosmetics or in pharmaceuticals.

Among these thickening agents, particularly exemplary are cellulose and derivatives thereof such as cellulose ethers, heterobiopolysaccharides such as xanthan gum, scleroglucans, and polyacrylic acids which either may or may not be crosslinked.

The thickening agents are preferably present in proportions ranging from 0.1% to 5% by weight approximately relative to the total weight of the composition.

Depending on the intended application of the subject compositions, one skilled in this art can easily select the particular compounds and adjuvants that are necessary and characteristically employed to formulate these compositions.

Among these adjuvants or additives, especially representative are preservatives, stabilizing agents, pH regulators, osmotic pressure modifiers, emulsifying agents, sunscreen agents, antioxidants, fragrances, colorants, anionic, cationic, nonionic, amphoteric or zwitterionic surface-active agents or mixtures thereof, polymers, and the like.

In addition to the particular antifungal/antibacterial species according to the invention, the subject compositions may also contain compounds already known for reducing or decelerating hair loss.

This invention also features a cosmetic treatment for the hair and/or the scalp, comprising applying thereto a composition as described above, for the purpose of reducing hair loss.

The preferred regime or regimen of application comprises applying 1 to 20 g of the composition to all or to certain parts of the scalp, at a frequency of one to two applications per day, for 1 to 7 days per week, for a period of time of from 1 to 6 months or even longer.

In order to further illustrate the present invention and the advantages thereof, the following specific examples are given, it being understood that same are intended only as illustrative and in nowise limitative.

EXAMPLE 1

A shampoo having the following composition was formulated:

| | |
|---|---|
| (a) Sodium lauryl ether sulfate containing 2.2 mol of ethylene oxide | 12 g |
| (b) Coconut monoisopropanolamide | 3.5 g |
| (c) Hydroxypropylcellulose quaternized with triethanolamine | 0.4 g |
| (d) 1-Hydroxy-4-methyl-6-(2,4,4-trimethylpentyl)-2-(1H)-pyridone, marketed under the trademark OCTOPIROX by Hoechst | 0.3 g |
| (e) Triclosan marketed under the trademark IRGASAN by Ciba-Geigy | 0.25 g |
| (f) Preservative | 0.3 g |
| (g) Fragrance | 0.4 g |
| (h) Water qs | 100 g |

When used regularly 2 to 3 times per week, this shampoo reduced hair loss, while at the same time improved the general appearance of the hair.

EXAMPLE 2:

A lotion for the scalp having the following composition was formulated:

| | |
|---|---|
| (a) Ethyl alcohol | 38 g |
| (b) Castor oil | 0.2 g |
| (c) Chorhexidine gluconate marketed by ICI | 0.4 g |
| (d) Undecylenic acid | 0.25 g |
| (e) Fragrance | 0.3 g |
| (f) Dye | 0.05 g |
| (g) Water qs | 100 g |

When applied daily to the scalp and the hair, without rinsing, this lotion reduced hair loss, while at the same time improved the general appearance of the hair.

EXAMPLE 3

A foam for the scalp having the following composition was formulated:

| | |
|---|---|
| (a) Diallyldimethyl ammonium chloride polymer marketed under the trademark MERQUAT 100 by Merck | 1.5 g |
| (b) Hydroxyethylcellulose and diallyldimethyl ammonium chloride copolymer marketed under the trademark CELQUAT LOR by National Starch | 0.3 g |
| (c) Quaternary ammonium salt marketed under the trademark ARQUAD 16-25W by AKZO | 0.3 g |
| (d) Silicon gum marketed under the trademark QC F2-1671 by Dow Corning | 0.1 g |
| (e) Propylene glycol | 5 g |
| (f) Phenoxyethanol | 0.4 g |
| (g) 1-Hydroxy-4-methyl-6-(2,4,4-trimethylpentyl)-2-(1H)-pyridone, marketed under the trademark OCTOPIROX by Hoechst | 0.2 g |
| (h) Chloramphenicol | 0.3 g |
| (i) Water qs | 100 g |

After regular application of this foam, a reduction in hair loss and an improvement in the general appearance of the hair were observed.

EXAMPLE 4

A spray for the scalp having the following composition was formulated:

| | |
|---|---|
| (a) Isoparaffin hydrocarbon (isobutane marketed by Hüls) | 0.5 g |
| (b) Polydimethylsiloxane marketed under the trademark DC 200 FLUID by Dow Corning | 1.2 g |
| (c) Polyaminosiloxane marketed under the trademark DC 929 EMULSION by Dow Corning | 0.4 g |
| (d) Ethanol | 15 g |
| (e) Crosslinked acrylic acid polymer marketed under the trademark CARBOPOL 980 by Goodrich | 0.1 g |
| (f) Triclosan marketed under the trademark IRGASAN by Ciba-Geigy | 0.35 g |
| (g) 1-Hydroxy-4-methyl-6-(2,4,4-trimethylpentyl)-2-(1H)-pyridone, marketed under the trademark OCTOPIROX by Hoechst | 0.1 g |
| (h) Undecylenic acid | 0.15 g |
| (i) Triethanolamine qs | pH 7 |
| (j) Water qs | 100 g |

This composition was packaged in a pump-dispenser bottle.

After regular application of this spray, a reduction in hair loss and an improvement in the general appearance of the hair were observed.

EXAMPLE 5:

A lotion for combating hair loss having the following composition was formulated

| | |
|---|---|
| (a) 1-(4-Chlorophenoxy)-1-(1H-imidazolyl)-3,3-dimethyl-2-butanone, marketed under the trademark CLIMBAZOLE by Bayer | 0.1 g |
| (b) Undecylenic acid | 0.15 g |
| (c) Ethanol | 38 g |
| (d) Fragrance qs | |
| (e) Dye qs | |
| (f) Water qs | 100 g |

When applied daily to the hair, without rinsing, this lotion reduced hair loss, while at the same time improved the general appearance of the hair.

EXAMPLE 6

Tests of effectiveness:

The following lotion was formulated in order to demonstrate the effectiveness of the compositions of the invention:

| | |
|---|---|
| (a) 1-Hydroxy-4-methyl-6-(2,4,4-trimethylpentyl)-2-(1H)-pyridone, marketed under the trademark OCTOPIROX by Hoechst | 0.25 g |
| (b) Triclosan marketed under the trademark IRGASAN by Ciba-Geigy | 0.3 g |
| (c) Ethanol | 45 g |
| (d) Fragrance qs | |
| (e) Water qs | 100 g |

This lotion was supplied to 20 male individuals displaying androgenic alopecia. They applied this composition to the scalp, without rinsing, once a day for 9 months. During the course of this study, a standardized questionnaire was periodically given to each individual.

The results obtained are reported in the tables below.

(A) Appearance of the hair:

These individuals described themselves in respect of the greasy, lackluster, sticky or normal nature of their hair.

The results collected are reported in Table I below:

TABLE I

| Time in Months | 0 | 0.5 | 1 | 1.5 | 2 | 3 | 4 | 5 | 6 | 7 | 8 | 9 |
|---|---|---|---|---|---|---|---|---|---|---|---|---|
| Greasy hair | 19 | 5 | 3 | 4 | 2 | 3 | 1 | 3 | 2 | 2 | 2 | 3 |
| Non-greasy hair | 1 | 15 | 17 | 16 | 18 | 17 | 19 | 17 | 18 | 18 | 18 | 17 |
| Lacklustre hair | 7 | 6 | 6 | 3 | 2 | 1 | 1 | 1 | 1 | 1 | 2 | 1 |
| Non-lacklustre hair | 13 | 14 | 14 | 17 | 18 | 19 | 19 | 19 | 19 | 19 | 18 | 19 |
| Sticky hair | 17 | 2 | 1 | 0 | 0 | 0 | 0 | 0 | 0 | 0 | 0 | 0 |
| Non-sticky hair | 3 | 18 | 19 | 20 | 20 | 20 | 20 | 20 | 20 | 20 | 20 | 20 |
| Normal hair | 1 | 13 | 16 | 16 | 18 | 17 | 16 | 16 | 17 | 17 | 18 | 18 |
| Abnormal hair | 19 | 7 | 4 | 4 | 2 | 3 | 4 | 4 | 3 | 3 | 2 | 2 |

It was observed that the very large majority of the individuals observed a general normalization in the state of their hair from the first weeks of treatment, especially as regards the greasy, lacklustre and sticky appearance thereof.

(B) Change in the seborrhoea:

These individuals evaluated the variations in their seborrhoea, which could be increased, stable or reduced. The results obtained are reported in Table II below:

TABLE II

| Time in Months | 0.5 | 1 | 1.5 | 2 | 3 | 4 | 5 | 6 | 7 | 8 | 9 |
|---|---|---|---|---|---|---|---|---|---|---|---|
| Increased seborrhoea | 3 | 1 | 0 | 0 | 0 | 0 | 1 | 0 | 0 | 1 | 0 |
| Stable seborrhoea | 15 | 11 | 14 | 15 | 14 | 14 | 12 | 13 | 12 | 11 | 10 |
| Reduced seborrhoea | 2 | 8 | 6 | 5 | 6 | 6 | 7 | 7 | 6 | 8 | 10 |

It was observed that after a transitory phase of increased seborrhoea in a minority of individuals, a normalization of the seborrhoea was established. No reactional seborrhoea was detected.

(C) Observation of pruritus:

These individuals reported the presence or absence of pruritus. The results obtained are reported in Table III below:

TABLE III

| Time in Months | 0 | 0.5 | 1 | 1.5 | 2 | 3 | 4 | 5 | 6 | 7 | 8 | 9 |
|---|---|---|---|---|---|---|---|---|---|---|---|---|
| Pruritus | 16 | 12 | 0 | 0 | 0 | 0 | 1 | 0 | 1 | 0 | 1 | 0 |
| Absence of pruritus | 4 | 8 | 20 | 20 | 20 | 20 | 19 | 20 | 19 | 20 | 19 | 20 |

It was observed that a very marked improvement was established from the first weeks of treatment.

(D) Observation of hair loss:

Hair loss was estimated by these individuals. At each consultation, envelopes containing hairs of a similar color to their own and of different amounts ranging from about 10 to about 150 were given to them. Each individual then indicated the envelope which corresponded best to the estimation of their hair loss during shampooing.

The results are given according to whether the hair loss increased, remained stable or was reduced over the course of the application/treatment.

These results obtained are reported in Table IV below:

TABLE IV

| Time in Months | 0.5 | 1 | 1.5 | 2 | 3 | 4 | 5 | 6 | 7 | 8 | 9 |
|---|---|---|---|---|---|---|---|---|---|---|---|
| Increased hair loss | 9 | 3 | 1 | 0 | 0 | 0 | 0 | 0 | 0 | 0 | 0 |
| Stable hair loss | 8 | 13 | 12 | 13 | 12 | 10 | 6 | 7 | 7 | 7 | 8 |
| Reduced hair loss | 3 | 4 | 7 | 7 | 8 | 10 | 14 | 13 | 13 | 13 | 12 |

For the majority of the individuals, a significant reduction in hair loss was observed after application of the composition for a few weeks. This reduction tended to stabilize after application for 5 to 6 months.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for reducing or decelerating hair loss from a human subject in need of such treatment, comprising topically applying a dermatological/cosmetic composition of matter comprising an effective hair loss-reducing amount of a combinatory immixture of (a) at least one antifungal agent and (b) at least one halogenated antibacterial agent other than a macrolide or pyranoside wherein said at least one antifungal agent is selected from the group consisting of 6-cyclohexyl-1-hydroxy-4-methyl-2(1H)-pyridone, 1-hydroxy-4-methyl-6- (2,4,4trimethylpentyl)-2-(1H)-pyridone and 1-(4-chlorophenoxy)-1-(1H-imidazolyl)- 3,3-dimethyl-2-butanone and said at least one halogenated antibacterial agent is selected from the group consisting of 5-chloro-2-(2,4dichlorophenoxy)phenol, chlorhexidine and chloramphenicol wherein from 0.01% to 5 5 by weight of said at least one antifungal agent and 0.01% to 10% by weight of said at least one halogenated antibacterial agent is contained in said composition.

2. The method as defined by claim 1, wherein from 0.1% to 2% by weight of said at least one antifungal agent (a) is contained in said composition.

3. The method as defined by claim 1, wherein from 0.1% to 2% by weight of said at least one halogenated antibacterial agent (b) is contained in said composition.

4. The method as defined by claim 1, wherein the weight ratio of said at least one antifungal agent contained in said topically administered composition (a) to said at least one halogenated antibacterial agent (b) ranges from 0.2 to 10.

5. The method as defined by claim 1, wherein said topically administered composition is formulated into a topically physiologically acceptable medium therefor.

6. The method as defined by claim 5, wherein said topically administered composition is selected from the group consisting of a lotion, shampoo, foam, cream, gel, ointment, salve, milk, stick, spray, balm, emulsion, powder, solid soap or liquid soap.

7. The method as defined by claim 6, said topically administered composition further comprising at least one topically pharmaceutically acceptable additive or adjuvant.

8. The method as defined by claim 7, wherein said at least one additive or adjuvant is selected from the group consisting of a thickening agent, preservative, stabilizer, pH regulator, osmotic pressure modifier, emulsifying agent, sunscreen agent, antioxidant, fragrance, colorant, polymer, surface-active agent and mixture thereof.

* * * * *